United States Patent [19]
Mayer et al.

[11] 3,975,452
[45] Aug. 17, 1976

[54] REPROCESSING OF FINAL ACID FROM NITROGLYCERINE PRODUCTION

[75] Inventors: Hans Rolf Jakob Mayer; Gerhard Langecker, both of Cologne; Hans-Jürgen Gebauer, Troisdorf, all of Germany

[73] Assignee: Firma Josef Meissner, Cologne, Germany

[22] Filed: June 27, 1974

[21] Appl. No.: 483,757

[30] Foreign Application Priority Data
June 29, 1973   Germany............................ 2333144

[52] U.S. Cl................................. 260/645; 260/467
[51] Int. Cl.$^2$........................................... C07C 79/10
[58] Field of Search............................ 260/467, 645

[56] References Cited
FOREIGN PATENTS OR APPLICATIONS
989,664   4/1965   United Kingdom................. 260/467

Primary Examiner—Leland A. Sebastian
Attorney, Agent, or Firm—Burgess, Dinklage & Sprung

[57] ABSTRACT

A process for treating final acid obtained in forming a nitrate of a polyhydric alcohol, said final acid comprising a mixture of sulfuric acid, nitric acid, water and said nitrate, said process comprising mixing said final acid with an aromatic nitro compound, allowing said mixture to stratify whereby said nitrate is dissolved into said aromatic nitro compound as one layer and there is another substantially nitrate-free waste acid layer comprising sulfuric acid, nitric acid and water, and separating said layers. Preferably the nitrate is trinitroglycerine and the aromatic nitro compound is dinitrotoluene. The waste acid layer advantageously is partially used to form additional dinitrotoluene and is partially mixed with fresh final acid since its presence serves to stabilize such final acid by preventing any settling out of trinitroglycerine, presumably by the action of the small amount of dinitrotoluene which may be present in said waste acid.

7 Claims, 2 Drawing Figures

REPROCESSING OF FINAL ACID FROM NITROGLYCERINE PRODUCTION

The safe reprocessing of the final acid obtained in the production of esters of nitric acid by nitration of polyhydric alcohols, in particular glycerine, ethylene glycol, or glycerine-glycol mixtures, is a long known problen.

The acid obtained, e.g. in nitroglycerine production, has the following approximate composition:

8–12% nitric acid,
2–3% nitroglycerine,
15–18% water,
balance sulfuric acid.

In prior art methods, the acid obtained after the separation of the reaction mixture by means of static or centrifugal separators, which still contained substantial amounts of nitric acid, is diluted. The solubility of the nitroglycerine in the acid is increased thereby and the dangerous precipitation of emulsified nitroglycerine is prevented, but the stability of the acid is impaired. The nitroglycerine in the diluted or undiluted acid is then destroyed by heating in a separate apparatus. The now nitroglycerine-free acid is freed from the produced nitrogen peroxide and nitric acid in a conventional manner, a 70 – 72% sulfuric acid or a concentrated acid being obtained depending on the method used. The reprocessing of nitroglycol and nitroglycerine nitroglycol final acids is conducted in a corresponding manner.

By using this method of treatment, the alcohol component of the esters of nitric acid is decomposed and destroyed whereas the nitrogen component together with the remaining nitric acid present in the acid is recovered after separation in expensive absorption devices in the form of nitric acid of different concentrations. In spite of the fact that to some extent safe handling of the final acids becomes possible if the individual operations are appropriately carried out, accidents and shutdowns have occasionally occurred. However, feasible alternatives were not available until now.

It is a primary object of the invention to recover in a utilizable condition the nitroglycerine emulsified or dissolved in the final acid and to allow the nitroglycerine-free waste acid to be profitably used. The process itself must be absolutely safe to operate.

These and other objects and advantages are realized in accordance with the present invention pursuant to which a final acid obtained in forming a nitrate of a polyhydric alcohol and comprising a mixture of sulfuric acid, nitric acid, water and said nitrate, is mixed with an aromatic compound, the mixture is allowed to stratify whereby said nitrate is dissolved into said aromatic nitro compound as one layer and there is another substantially nitrate-free waste acid layer comprising sulfuric acid, nitric acid and water, and said layers are separated.

For the sake of simplicity, this process will be described hereinbelow with reference to the final acid obtained in the production of nitroglycerine; however, it equally applies to other esters of nitric acid and polyhydric alcohols, especially alkylene glycols, such as nitro-glycol, dinitrochlorohydrin, diethylene glycol dinitrate, triethylene glycol dinitrate and mixtures thereof which are important in the explosives industry.

The aromatic nitro compounds suitable for the extraction of nitroglycerine and other esters of nitric acid from the final acids, which may be used in the production of explosives, are of the kind which are liquid either at room temperature or moderately elevated temperature of up to about 70°C. Appropriate nitro compounds are, for example, mixtures of the other trinitrotoluene isomers obtained in the refining of 2,4,6-trinitrotoluene, the so-called drip oils, the so-called dynamite-TNT, a non-refined commercial trinitrotoluene, low-melting products of dinitrotoluene production, dinitrotoluenes, and isomeric mixtures thereof such as are produced in the nitration of toluene or nitrotoluenes or in the isomeric separation for the preparation of powder dinitrotoluene, nitrobenzenes, nitroxylenes, nitroalkylbenzenes, and nitronaphthalenes. However, dinitrotoluenes are preferably used for the purposes of the invention. The quantitative ratio of final acids to aromatic nitro compounds, in particular dinitrotoluene, which serve as extracting agents, is on the order of about 1 to 20:1, i.e. up to the 20-fold volume of final acid or more can be extracted with the liquid dinitrotoluene. It is of primary importance that the extracts exhibit an adequately high DNT-content in order to be stabilized. As soon as the aromatic nitro compounds come into contact with the nitroglycerine-containing final acid, the acid itself is stabilized and, hence, the extraction may be conducted without danger. Furthermore, it is preferable for the extraction to use those aromatic nitro compounds which are not further nitrated under the extraction conditions because such a reaction during extraction might result in a decomposition of the nitroglycerine or the other esters of nitric acid.

A particularly safe handling is guaranteed if the waste acid remaining after the separation of the nitroglycerine-loaded aromatic nitro compound, which contains dissolved therein certain amounts of aromatic nitro compounds such as dinitrotoluene, is used for stabilizing other nitroglycerine-containing final acid prior to extraction by mixing the final acid with an equal or larger volume of the waste acid having dissolved therein dinitrotoluene or other aromatic nitro compound.

According to the preferred embodiment of the process of the invention, the waste acid obtained in the extraction, which is free from the nitration product, in particular nitroglycerine, is utilized for the nitration of aromatic compounds or aromatic nitro compounds, especially for the preparation of that aromatic nitro compound which serves as extracting agent in the process of the invention. It is preferable to employ as raw materials for the nitration those aromatic compounds and aromatic nitro compounds which upon further nitration yield aromatic nitro compounds suitable for use in different proportions together with nitroglycerine or other esters of nitric acid in specific kinds of explosives. For example, the nitroglycerine present in the final acid is extracted with dinitrotoluene and the resultant waste acid is utilized for the preparation of dinitrotoluene by taking advantage of the nitric acid and sulfuric acid still contained therein, the so-obtained dinitrotoluene being used for the extraction of the nitroglycerine from other final acid which nitroglycerine is then recovered as a solution in dinitrotoluene. This process and those described hereinbelow utilizing dinitrotoluene as extracting agent may be conducted in a similar manner, either batchwise or continuously, with other suitable aromatic nitro compounds used in the manufacture of explosives.

Since it was found that together with the nitroglycerine substantial amounts of nitric acid were also extracted by the dinitrotoluene from the nitroglycerine-containing final acid, it has proved advantageous to prewash the solution of nitroglycerine in dinitrotoluene with water before neutralizing this extract with soda solution or other suitable alkalis such as bicarbonates or ammonia water. The diluted nitric acid obtained in the extraction with water is advantageously returned to the dinitrotoluene production process, thus avoiding nitric acid losses.

In carrying out the process of the invention, it is not decisive whether the extraction of nitroglycerine from the nitroglycerine-containing final acid is conducted in one stage or in a plurality of stages, whether the dinitrotoluene utilized for extraction has an isomeric composition which differs from what is conventionally used, or whether the dinitrotoluene is obtained in a batch or continuous process, cocurrently, counter-currently or a combination of the two methods; furthermore, the kind and method of washing and drying of the resultant solution of nitroglycerine in dinitrotoluene is not critical.

The process of the invention will be better understood from the drawings wherein.

Figure 1:
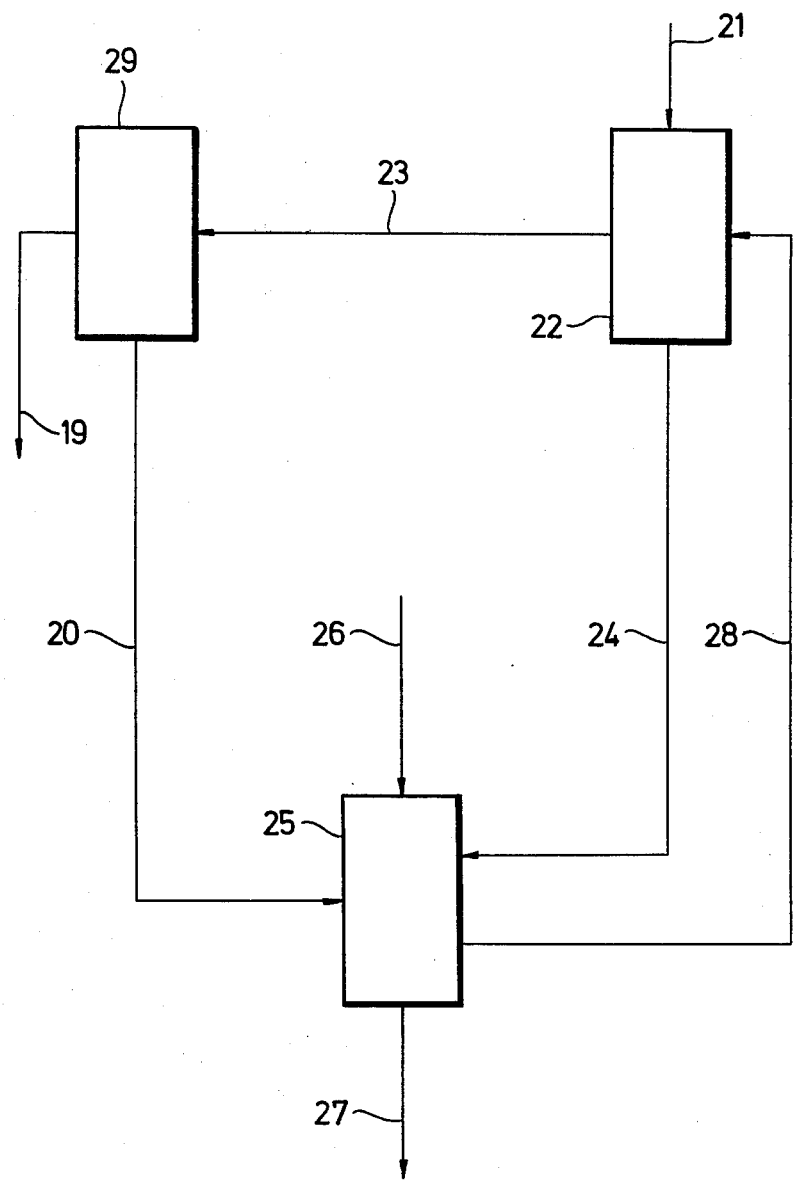
FIG. 1 is a simplified diagrammatic flow sheet of the process.

Referring now more particularly to the drawings, in FIG. 1 a solution or suspension of nitroglycerine-containing final acid obtained in the nitration of glycerine is fed through conduit 21 to an extractor 22 wherein it is extracted with dinitrotoluene supplied by conduit 28 and the nitroglycerine is thereby stabilized. The nitroglycerine-containing dinitrotoluene leaves the extractor 22 through conduit 23 and is neutralized by washing with water and soda solution in washing apparatus 29, dried and removed from the system at 19. The nitroglycerine waste acid in which nitroglycerine is no longer detectable is passed from extractor 22 through conduit 24 to a dinitrotoluene production unit 25 into which toluene or mononitrotoluene are introduced through conduit 26. The resultant mononitrotoluene waste acid or dinitrotoluene waste acid leaves unit 25 through conduit 27, the produced dinitrotoluene being fed through conduit 28 to extractor 22. The diluted nitric acid obtained in washing the nitroglycerine-containing dinitrotoluene with water in washer 29 is returned through conduit 20 to the dinitrotoluene production unit 25 in order to avoid nitric acid losses.

By adding further nitric acid, and sulfuric acid if necessary, it is possible to produce more dinitrotoluene in the dinitrotoluene production unit 25 than by utilizing only the nitric and sulfuric acid from the nitroglycerine final acid, and to employ some or all of the dinitrotoluene for the extraction of the nitroglycerine final acid and to operate the plant without nitroglycerine final acid for producing nitroglycerine-free dinitrotoluene.

One of the possible embodiments of the process according to the invention which illustrates the advantages of a continuous process is described in FIG. 2 and in the following examples. The apparatus comprises an extraction stage, a stage for mononitration of toluene and another stage for further nitration to dinitrotoluene.

Nitroglycerine-containing final acid obtained in nitroglycerine production is run through line 101 into the holding tank 1 where it is mixed with nitroglycerine-free waste acid from an extractor 17 and a separator 18 coming from the overflow 102 of a receiver 2. Thus, the nitroglycerine waste acid, freed of nitroglycerine and saturated with dinitrotoluene, prevents the precipitation of undissolved nitroglycerine during storage in container 1 and stabilizes the nitroglycerine present in the nitroglycerine-containing final acid owing to the dinitrotoluene contained therein.

The raw materials run from the receivers for nitroglycerine final acid 2, water 3, and toluene 4 into a metering apparatus 5 which allows the exact regulation of the required mass flow and maintains the same at a constant rate.

For the nitration of the toluene to dinitrotoluene, an arrangement known per se was selected wherein the acid streams and product streams run in a parallel direction within the individual stages but in a countercurrent direction as they proceed from stage to stage. Accordingly, the toluene from receiver 4 — through metering apparatus 5 and line 103 — and mononitrotoluene final acid from a separator 12 through line 104 are first transferred to a stirring apparatus 6 in order to use up the remaining nitric acid and to extract the dissolved mononitrotoluene. The emulsion overflows through line 105 into separator 7 which may be a static or centrifugal separator. The mononitrotoluene waste acid is transferred to a waste acid storage tank (not shown) through line 106 while the toluene flows through line 107 into the main nitration apparatus 8 of the mononitrator into which there are simultaneously fed through line 108 diluted nitric acid from an extractor 10 obtained and recovered in a separator 11 and dinitrotoluene final acid through line 109 from a dinitrotoluene stage 15 separated from dinitrotoluene in a separator 16.

After completion of the nitration in apparatus 9, the reaction mixture is separated in a separator 12 into raw mononitrotoluene and mononitrotoluene final acid which may be accomplished statically such as in separators 7, 11, 16, 18, or by means of a centrifugal separator, or by other methods. As already described above, the mononitrotoluene-final acid is fed via line 104 to stirring apparatus 6, the raw mononitrotoluene via line 110 to the main nitrating apparatus 13 of the dinitrotoluene stage into which nitroglycerine waste acid from receiver 2 is simultaneously introduced by passing through metering apparatus 5 and line 111. The nitration mixture passes through the renitrating apparatuses 14 and 15 in which the conversion to dinitrotoluene is completed. It is separated in separator 16, and, as set forth above, the dinitrotoluene-final acid is fed into apparatus 8 of the mononitration via line 109 and the dinitrotoluene via line 112 into extractor 17 in which the nitroglycerine is extracted from the acid mixture supplied via line 113 from holding tank 1. Subsequent to the separation of the phases in separator 18, the nitroglycerine waste acid runs back via line 114 through receiver 2 and into holding tank 1 via line 102 while the solution of nitroglycerine in dinitrotoluene is washed in extractor 10 with water supplied from receiver 3 through the metering apparatus 5 and line 115 in order to recover the nitric acid which had been extracted together with the nitroglycerine. From separator 11, the nitric acid runs via line 108 into apparatus 8 of the mononitrator, and the solution of nitroglycerine in dinitrotoluene leaves the system at 116 later to be washed in a washing plant and subsequently dried (not shown).

In carrying out the process, centrifugal separators were used as separators in items 7, 12, and 16; a fractionating pump as the metering apparatus 5; and heatable stirrer vessels provided with special separators for extraction and separation of the phases were employed in 10 and 17, 11 and 18. Containers provided with cooling coils and jacket and equipped with a strong agitator, so-called "pot apparatus", were utilized as nitrating apparatuses 6, 8, 9 and 13, 14, 15.

The solutions of nitroglycerine in dinitrotoluene obtained were once more washed with water, twice with soda solution, then washed again with water to remove the last traces of alkali and were subsequently dried in vacuum.

An extension of the above-described plants by providing receivers for nitric acid and sulfuric acid as well as a corresponding metering device makes it possible to introduce additional amounts of acid into the nitrating apparatus, advantageously into the main nitrating apparatus 13 of the dinitrator and the main nitrating apparatus 8 of the mononitrator, and, consequently, by increasing the utilized amount of toluene, an accordingly larger amount of dinitrotoluene can be produced than the amount corresponding to the original nitric acid and sulfuric acid-content of the nitroglycerine-final acid. The dinitrotoluene so obtained is again utilized for extracting nitroglycerine from the acid container 1. If more dinitrotoluene is produced than is needed, a portion may be tapped off from separator 16, this portion being free of nitroglycerine.

The process of the invention is illustrated in the following examples wherein it was first carried out batchwise, the required nitroglycerine-final acid being obtained in the nitration of glycerine in laboratory equipment, the so-called Schlegel-apparatus, according to conventional methods. The nitroglycerine content of this acid was in the range of 2–3% by weight.

EXAMPLE 1

200 g of nitroglycerine-final acid comprising 75.3% sulfuric acid, 8.9% nitric acid and 0.27% nitric oxides were mixed for 10 minutes at 60°C with 64 g of dinitrotoluene having a solidification point of 56.4°C and the two phases were subsequently separated.

After washing and drying, the dinitrotoluene contained 8.0% nitroglycerine, at a solidification point of 52.4°C. The lowering of the solidification point was confirmed by the addition of the corresponding amount of nitroglycerine to the dinitrotoluene used for extraction. Nitroglycerine could not be detected in the resultant waste acid which contained 76.8% sulfuric acid, 6.0% nitric acid and 0.29% nitric oxides.

EXAMPLE 2

The extraction of a nitroglycerine-final acid comprising 72.1% sulfuric acid, 12.5% nitric acid and 0.25% nitric oxides under the conditions of Example 1 with 64 g of dinitrobenzene resulted in a waste acid in which nitroglycerine could not be detected. The waste acid contained 74.2% sulfuric acid, 7.0% nitric acid and 0.19% nitric oxides. The dinitrobenzene had extracted 8.8% nitroglycerine.

EXAMPLE 3 a. 318.5 g of nitroglycerine-final acid comprising 70.4% sulfuric acid, 12.0% nitric acid and 0.28% nitric oxides was stirred with 102.5 g of dinitrotoluene (solidification point 56.4°C) for 30 minutes at 60°C and the phases were separated. The dinitrotoluene obtained having a solidification point of 52.85°C, contained 7.3% nitroglycerine.

b. 40 g of a mononitrotoluene-isomeric mixture were dropped within 14 minutes under vigorous stirring as in Example 1 into 301 g of the nitroglycerine-free waste acid obtained according to (a) comprising 6.6% nitric acid; the stirring was continued for another 20 minutes and the phases were separated.

c. 60 g of acid dinitrotoluene obtained according to (b) were reacted with 190 g nitroglycerine-final acid (72.1% sulfuric acid, 12.4% nitric acid and 0.3% nitric oxides) from a further Schlegel-nitration, stirred for 30 minutes at 60°C, and the phases separated.

The dinitrotoluene so obtained had a nitroglycerine content of 7.2% and a solidification point of 52.9°C.

The stirred waste acid contained 74.4% sulfuric acid, 6.1% nitric acid and 0.3% nitric oxides. Again, nitroglycerine could not be detected.

EXAMPLE 4

Figure 2:
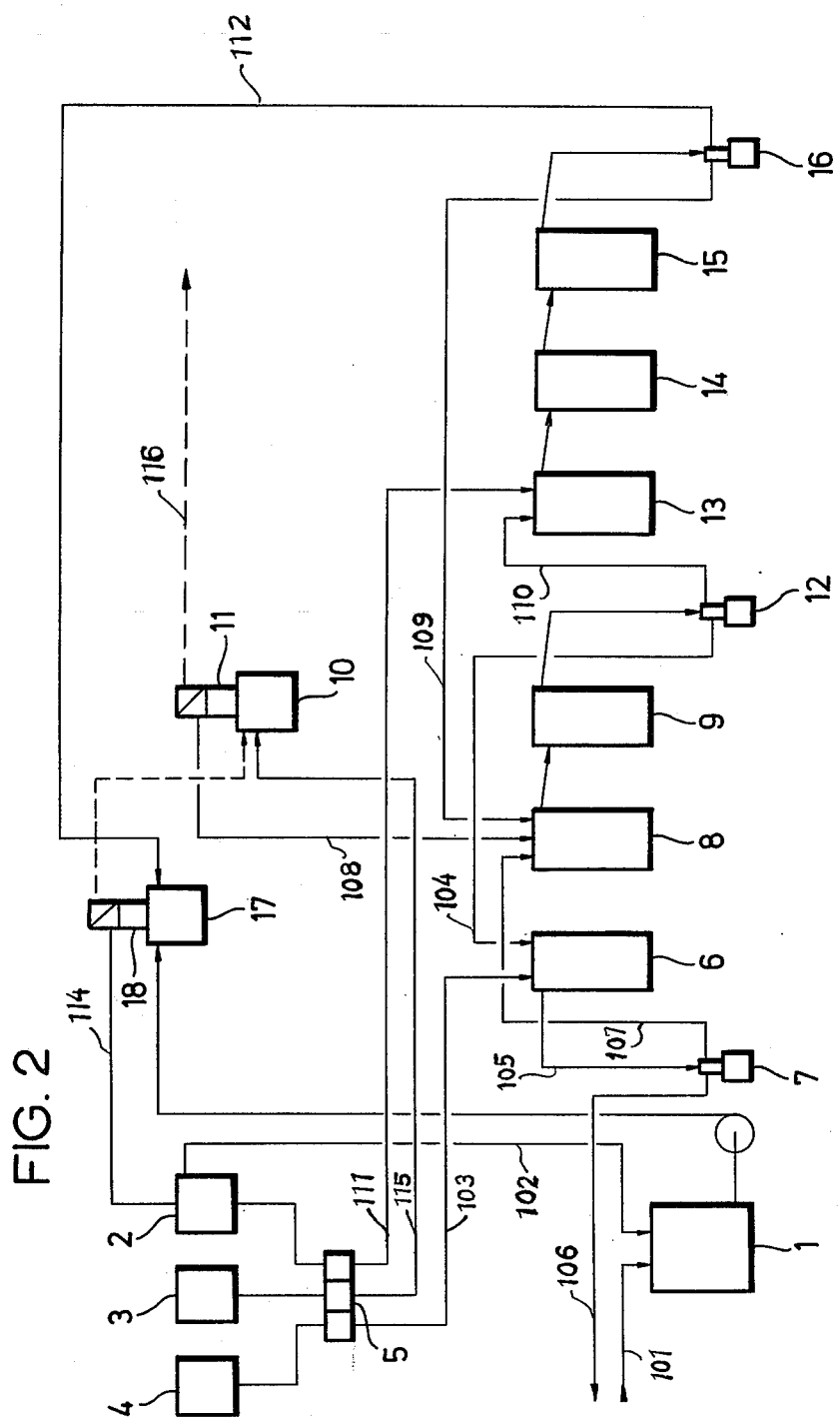
FIG. 2 is a flow sheet of a continuous process for carrying out the invention

In an apparatus corresponding to FIG. 2 provided with an additional receiver and metering apparatus for a 98 weight % nitric acid, 15.2 kg/h of a nitroglycerine-final acid comprising 70.5% sulfuric acid, 11.8% nitric acid and 0.22% nitric oxides, after reaching a steady state, were fed to the stabilized acid in container 1. About 20 kg/h were discharged from this container and the stabilized acid was fed to the extractor 17, extraction with the produced dinitrotoluene followed and, after separation of the phases in 18, the nitroglycerine-free acid was piped into receiver 2. There, the amount necessary for the toluene nitration was withdrawn and metered into the main nitrating apparatus 13 of the dinitration stage. The excess nitroglycerine-free acid was again returned to container 1 for stabilizing the nitroglycerine-final acid.

At the same time, 0.44 kg/h of water were discharged from receiver 3 and fed by means of 5 into the extractor 10, the nitroglycerine-containing dinitrotoluene was subjected to a preliminary washing and, after separation of the phases in 11, the diluted nitric acid was piped into the main nitrating apparatus 7 of the mononitration stage while the nitroglycerine-containing dinitrotoluene was collected for washing. 1.12 kg/h of a 98 weight % nitric acid from the nitric acid receiver were metered into apparatus 7 and 1.86 kg/h of toluene from receiver 4 were metered into 6. At this stage, the temperatures in the apparatuses 6, 8, 9 and 13, 14, 15 were about 30° – 45°C and 55° – 70°C, respectively.

According to this method of operation, 14.5 kg of mononitrotoluene waste acid comprising 72.7% sulfuric acid, 0.05% nitric acid and 0.33% nitric oxides were obtained whereas the acid nitroglycerine-containing dinitrotoluene was first collected and subsequently washed, at first with water, then twice with an approximately 5% soda solution and again with water to remove the alkali, and dried in vacuum. The output was about 3.75 kg/h with a nitroglycerine-content of 8.0% at a solidification point of 52.38°C.

It will be appreciated that the instant specification and examples are set forth by way of illustration and not limitation, and that various modifications and changes may be made without departing from the spirit and scope of the present invention.

What is claimed is:

1. A process for treating final acid obtained in forming a nitrate of a polyhydric alcohol, said final acid comprising a mixture of sulfuric acid, nitric acid, water and said nitrate, said process comprising mixing said final acid with a stabilizing agent comprising a waste acid with a nitro-aromatic compound selected from the group consisting of nitrobenzene, nitrotoluene, nitroxylene, nitronaphthalene or nitroalkylbenzene and then with one of said nitro-aromatic compounds as an extractant, allowing said mixture to stratify whereby said nitrate is dissolved into said nitro-aromatic compound as one layer and there is another substantially nitrate-free waste acid layer comprising sulfuric acid, nitric acid and water, separating said layers, and contacting at least a portion of said waste acid layer with an aromatic compound selected from the group consisting of benzene, toluene, xylene, naphthalene, alkylbenzene, nitrobenzene, nitrotoluene, nitroxylene, nitronaphthalene and nitroalkylbenzene to effect nitration thereof, a portion of said waste acid layer being combined with fresh final acid prior to mixing of said fresh final acid with said nitro-aromatic compound, said waste acid thereby serving as the stabilizing agent for said fresh final acid.

2. The process of claim 1, wherein the aromatic nitration product from said waste acid is said nitro-aromatic compound, said aromatic nitration product being recycled at least in part for mixing with a further quantity of said final acid.

3. The process of claim 1, wherein said polyhydric alcohol is glycerine.

4. The process of claim 1, wherein said nitro-aromatic compound is dinitrotoluene substantially free of mononitrotoluene and said nitration is effected at a temperature about 55° 70°C.

5. The process of claim 1, wherein said layer of nitro-aromatic compound and nitrate is washed with water to remove therefrom nitric acid dissolved therein.

6. The process of claim 1, wherein the weight of waste acid is at least equal to the volume of fresh final acid with which it is combined for stabilization.

7. The process of claim 6, wherein said polyhydric alcohol is glycerine, said nitrate of said polyhydric alcohol is trinitroglycerine, said nitro-aromatic compound is dinitrotoluene and it is mixed with about 1 to 20 times it volume of final acid, including the further steps of washing the layer of dinitrotoluene and trinitroglycerine with water to remove therefrom nitric acid dissolved therein, and contacting at least a portion of the waste acid layer with toluene or mononitrotoluene at a temperature of about 55 to 70°C to form dinitrotoluene substantially free of mononitrotoluene, and recycling said dinitrotoluene at least in part for mixing with a further quantity of said final acid.

* * * * *